(12) United States Patent
Takizawa et al.

(10) Patent No.: US 8,017,077 B2
(45) Date of Patent: Sep. 13, 2011

(54) STAINING AND STICKING SYSTEM

(75) Inventors: Seiichi Takizawa, Chikuma (JP); Atsuo Ito, Chikuma (JP); Tadashi Tofukuji, Chikuma (JP)

(73) Assignees: Sakura Seiki Co., Ltd., Nagano (JP); Sakura Finetek Japan Co., Ltd., Tokyo (JP)

( * ) Notice: Subject to any disclaimer, the term of this patent is extended or adjusted under 35 U.S.C. 154(b) by 679 days.

(21) Appl. No.: 12/084,896

(22) PCT Filed: Nov. 14, 2006

(86) PCT No.: PCT/JP2006/322603
§ 371 (c)(1),
(2), (4) Date: May 13, 2008

(87) PCT Pub. No.: WO2007/055366
PCT Pub. Date: May 18, 2007

(65) Prior Publication Data
US 2009/0098646 A1   Apr. 16, 2009

(30) Foreign Application Priority Data

Nov. 14, 2005  (JP) ................................. 2005-328869

(51) Int. Cl.
*G01N 21/00* (2006.01)
(52) U.S. Cl. ................ 422/65; 422/62; 422/63; 422/67; 422/500; 422/68.1
(58) Field of Classification Search ............ 422/99–100, 422/62–67, 68.1, 500
See application file for complete search history.

(56) References Cited

U.S. PATENT DOCUMENTS

| 5,625,706 A | 4/1997 | Lee et al. | |
|---|---|---|---|
| 2003/0049104 A1* | 3/2003 | Thiem et al. | ............ 414/267 |
| 2003/0049172 A1 | 3/2003 | Thiem | |

FOREIGN PATENT DOCUMENTS

| JP | 4-318441 A | 11/1992 |
|---|---|---|
| JP | 6-100522 B2 | 12/1994 |
| JP | 11-506196 A | 6/1999 |
| JP | 2001-2731 A | 1/2001 |
| JP | 2003-149102 A | 5/2003 |
| JP | 2005-300323 A | 10/2005 |

* cited by examiner

*Primary Examiner* — Jyoti Nagpaul
(74) *Attorney, Agent, or Firm* — Birch, Stewart, Kolasch & Birch, LLP

(57) ABSTRACT

The staining and sticking system includes a staining device and a sticking device provided separately from the staining device. The staining device stains a specimen in a predetermined color by dipping a basket containing a glass slide with the specimen in a plurality of tubs sequentially. The sticking device sticks a cover film piece onto the stained specimen on the glass slide, which has been taken out of the basket transferred from the staining device by transfer means. A staining control unit and a sticking control unit are interconnected so as to communicate with each other. Sticking condition data, related to the basket fed from the staining device, out of staining condition data and sticking condition data inputted to the staining control unit correspondingly to baskets, are sent from the staining control unit to the sticking control unit, and then the sticking device sticks the cover film piece.

7 Claims, 14 Drawing Sheets

FIG.16A

| START TUB | BASKET | STAINING CONDITION DATA | | | | STICKING CONDITION DATA | | |
|---|---|---|---|---|---|---|---|---|
| | | FIRST | SECOND | THIRD | FOURTH | AMOUNT OF MOUNTING MEDIUM | STICKING SPEED | LENGTH OF COVER FILM PIECE |
| 18a | A TISSUE DIAGNOSIS | FIRST TUB 10 MINUTES | THIRD TUB 5 MINUTES | SEVENTH TUB 20 MINUTES | TENTH TUB 3 MINUTES | 5 | 5 | 60 mm |
| 18b | B CYTOLOGIC DIAGNOSIS | FIRST TUB 5 MINUTES | FOURTH TUB 10 MINUTES | EIGHTH TUB 5 MINUTES | | 10 | 3 | 50 mm |
| 18c | C TISSUE DIAGNOSIS | FIRST TUB 10 MINUTES | THIRD TUB 5 MINUTES | SEVENTH TUB 20 MINUTES | NINETH TUB 3 MINUTES | 5 | 5 | 45 mm |

NOTE) AMOUNT OF MOUNTING MEDIUM : INDICATED BY NUMBER OF STAGES DIVIDED INTO TEN (AMOUNT IS INCREASED WITH INCREASING NUMBER THEREOF)

STICKING SPEED : INDICATED BY NUMBER OF STAGES DIVIDED INTO FIVE (SPEED IS INCREASED WITH INCREASING NUMBER THEREOF)

FIG.16B

| START TUB | BASKET | GLASS SLIDE No. | AMOUNT OF MOUNTING | STICKING SPEED | LENGTH OF COVER FILM PIECE |
|---|---|---|---|---|---|
| 18a | A TISSUE DIAGNOSIS | No. 1 | 5 | 5 | 60 mm |
| | | No. 2 | 4 | 4 | 50 mm |
| | | No. 3 | 5 | 3 | 45 mm |
| | | No. 4 | 4 | 5 | 50 mm |

# STAINING AND STICKING SYSTEM

FIELD OF TECHNOLOGY

The present invention relates to a staining and sticking system, more precisely relates to a staining and sticking system comprising: a staining device for staining a sliced specimen, which is stuck on a glass slide, in a predetermined color; and a sticking device for sticking a cover film piece or a cover glass onto the stained specimen on the glass slide.

BACKGROUND TECHNOLOGY

In inspecting sections of hospitals, laboratories, etc., a sliced specimen is stuck onto a glass slide and stained in a predetermined color, and then a cover film piece or a cover glass is stuck onto the stained specimen for microscopic observation. Staining the specimen and sticking the cover film piece or the cover glass are usually performed by specialized devices.

A staining device and a sticking device are separately installed, so the glass slide, on which the specimen stained by the staining device has been stuck, is manually transferred to the sticking device.

To improve staining and sticking efficiencies, perfectly automating the sequential staining and sticking works is required.

To fulfill the requirement, a staining and sticking system, whose casings are arranged to partially contact each other, is disclosed in Patent Document 1.

The disclosed staining and sticking system comprises: a staining device for staining a sliced specimen in a predetermined color by sequentially dipping a rack (basket), which contains a glass slide with the specimen, in a plurality of tubs, in which liquids for staining and cleaning the specimen are stored, with a robot arm; and a sticking device for sticking a cover glass onto the stained specimen on the glass slide, which has been taken out of the basket transferred by the robot arm of the staining device.

DISCLOSURE OF THE INVENTION

In the staining and sticking system disclosed in Patent Document 1, the basket containing the glass slide with the stained specimen can be transferred to the sticking device without manual operation, so that a work load of an operator can be lightened.

However, the staining device and the sticking device are independently arranged in the conventional staining and sticking system, control units thereof are also independently provided. With this structure, when the basket, which contains the glass slide with the specimen to be stained, is fed to the staining device, the operator must input staining condition data to the staining control unit of the staining device and separately input sticking condition data for the stained specimen, which has been stained under the staining conditions, to the sticking control unit.

As described above, in the staining and sticking system disclosed in Patent Document 1, the staining condition data and the sticking condition data are manually inputted to the control units of the staining device and the sticking device respectively. If the operator forgets to input the sticking condition data to the sticking control unit of the sticking device, the sticking work for sticking the cover glass onto the stained specimen must be stopped until the operator inputs the sticking condition data to the sticking device, further the staining work must be stopped.

It is usually difficult for the operator to determining the timing of inputting the sticking condition data to the sticking device due to relation with the timing of feeding the basket, which contains the glass slide with the specimen (the stained specimen), from the staining device to the sticking device. In case of frequently changing the sticking conditions, the work efficiency of the staining and sticking system must be lowered. To improve the work efficiency of the staining and sticking system, it is necessary to continuously feed the baskets, which contain the glass slides with the specimens onto which the cover glasses will be stuck under the same sticking conditions, to the sticking device. However, it is difficult for even the expert operator to continuously take out the baskets, which contain the glass slides with the specimens onto which the cover glasses will be stuck under the same sticking conditions, from the staining device.

These days, in the staining device, various kinds of liquids, e.g., a plurality of kinds of staining liquids, a cleaning liquid, are stored in a plurality of tubs so as to simultaneously stain specimens by dipping a plurality of baskets, each of which contains glass slides with the specimens, in the predetermined tubs. In some cases, the staining work of the basket latterly fed is performed prior to that of the basket formerly fed. Even if the operator inputs the staining condition data of the baskets to the control unit of the staining device when the baskets are fed to the staining device, the order of terminating the staining works of the baskets is not fixed, so the operator cannot input the sticking condition data to the control unit of the sticking device. Therefore, the operator must input the sticking condition data to the control unit of the sticking device after the basket is fed from the staining device to the sticking device.

If the operator delays to input the sticking condition data, the start of the sticking work for the basket fed from the staining device, which is performed by the sticking device, is delayed, and the baskets are dipped in the liquid tubs for more than the scheduled time or the baskets, which have been dipped in the liquid tubs for the scheduled time and taken out therefrom, are held in the air, so the stained specimens will be badly influenced.

Thus, the operator should input the sticking condition data to the control unit of the sticking device at the right time with respect to the progress of the staining work performed by the staining device, and the operator should carefully watch the termination of the staining work, etc., so lightening the work loads of the staining and sticking works are limited.

An object of the present invention is to provide a staining and sticking system, which is composed of a staining device and a sticking device separated from the staining device, capable of lightening the work loads of the staining and sticking works and can be downsized.

The inventors of the present invention tried to attach a transponder, in which staining condition data and sticking condition data are previously stored as digital data, to a basket, which contains glass slides with specimens to be stained, and read the data, by control units of a staining device and a sticking device, from the transponder so as to omit the data-input work.

However, data storing means, which stores the staining condition data and the sticking condition data, must be provided to the transponder, data reading means, which reads the data from the transponder, must be provided to the control units, so the staining and sticking system must be complexified and grown in size.

Generally, baskets containing glass slides with specimen are fed to the staining device by an operator, so if the operator inputs staining condition data and sticking condition data to a control unit of the staining device, the work load can be lighter than that in the case of separately inputting the staining condition data and the sticking condition data to the staining device and the sticking device.

Further, by interconnecting the staining control unit of the staining device and the sticking control unit of the sticking device so as to communicate with each other, the sticking condition data, which have been inputted to the staining control unit, can be sent to the sticking control unit of the sticking device, and the staining work can be smoothly performed in the multi-staining device by relating the baskets to the staining condition data and the sticking condition data, so that the inventors reach the present invention.

Namely, the staining and sticking system of the present invention comprises: a staining device for staining a sliced specimen in a predetermined color by sequentially dipping a basket, which contains one or a plurality of glass slides with the specimen, in a plurality of tubs, in which liquids for staining the specimen are stored; and a sticking device for sticking a cover film piece or a cover glass onto the stained specimen on the glass slide, which has been taken out of the basket transferred from the staining device by transfer means, the system is characterized in that a staining control unit of the staining device and a sticking control unit of the sticking device are interconnected so as to communicate with each other, that staining condition data and sticking condition data for each of baskets fed to the staining device are inputted to the staining control unit, the staining device sequentially dips the fed basket into the tubs on the basis of the staining condition data relating to the fed basket, and that the sticking device sticks the cover film piece or the cover glass onto the stained specimen on the glass slide, which has been contained in the fed basket, on the basis of the sticking condition data, which relate to the basket fed from the staining device and which has been sent from the staining control unit to the sticking control unit.

Preferably, the staining condition data and the sticking condition data are inputted to the staining control unit before starting the staining work, so that the work load of an operator can be lighter than that in the case of separately inputting the staining condition data and the sticking condition data.

Preferably, the sticking condition data of the basket fed from the staining device are sent from the staining control unit to the sticking control unit by the time of firstly taking out the glass slide from the fed basket.

Preferably, at least parts of casings of the staining device and the sticking device contact each other, so that the basket can be transferred from the staining device to the sticking device by the transfer means provided in the staining device or the sticking device.

Preferably, the transfer means transfers the basket, which contains the glass slide with the stained specimen, in a state of being dipped in a protective solution for protecting the specimen, so that transmutation of the specimen, which is caused by contacting the air during the transfer process, can be prevented.

Preferably, the basket, which contains the glass slide with the stained specimen, is inserted in a movable tub, in which a protective solution for protecting the specimen is stored, and transferred together with the movable tub.

The staining and sticking system of the present invention comprises: the staining device for staining the sliced specimen in the predetermined color by sequentially dipping the basket, which contains one or a plurality of the glass slides with the specimens, in a plurality of the tubs, in which the liquids for staining the specimens are stored; and the sticking device for sticking the cover film piece or the cover glass onto the stained specimen on the glass slide, which has been taken out of the basket transferred from the staining device by the transfer means. With this structure, the basket, which contains the glass slide with the specimen, can be automatically transferred to the sticking device after staining the specimen in the staining device, and then the cover film piece or the cover glass can be stuck onto the stained specimen.

Further, in the staining and sticking system of the present invention, the staining control unit of the staining device and the sticking control unit of the sticking device are interconnected so as to communicate with each other, the staining condition data and sticking condition data for each of the baskets fed to the staining device are inputted to the staining control unit, the staining device sequentially dips the fed basket into the tubs on the basis of the staining condition data relating to the fed basket, and the sticking device sticks the cover film piece or the cover glass onto the stained specimen on the glass slide, which has been contained in the fed basket, on the basis of the sticking condition data, which relates to the basket fed from the staining device and which has been sent from the staining control unit to the sticking control unit.

Therefore, by storing the staining condition data and the sticking condition data, which relate to the basket, in the staining control unit, the work of manually inputting the sticking condition data of the basket to the sticking control unit can be omitted, so that the work load of the operator can be lightened.

Unlike the conventional system including a transponder for storing the staining condition data and the sticking condition data as digital data, data storing means for storing the digital data in the transponder and data reading means for reading the digital data from the transponder can be omitted, so that the staining and sticking system of the present invention can be simplified and downsized.

BRIEF DESCRIPTION OF THE DRAWINGS

FIGS. 16A and 16B show examples of staining condition data and sticking condition data inputted to an input section of a staining control unit 10A.

OPTIMUM EMBODIMENTS OF THE INVENTION

Figure 1:
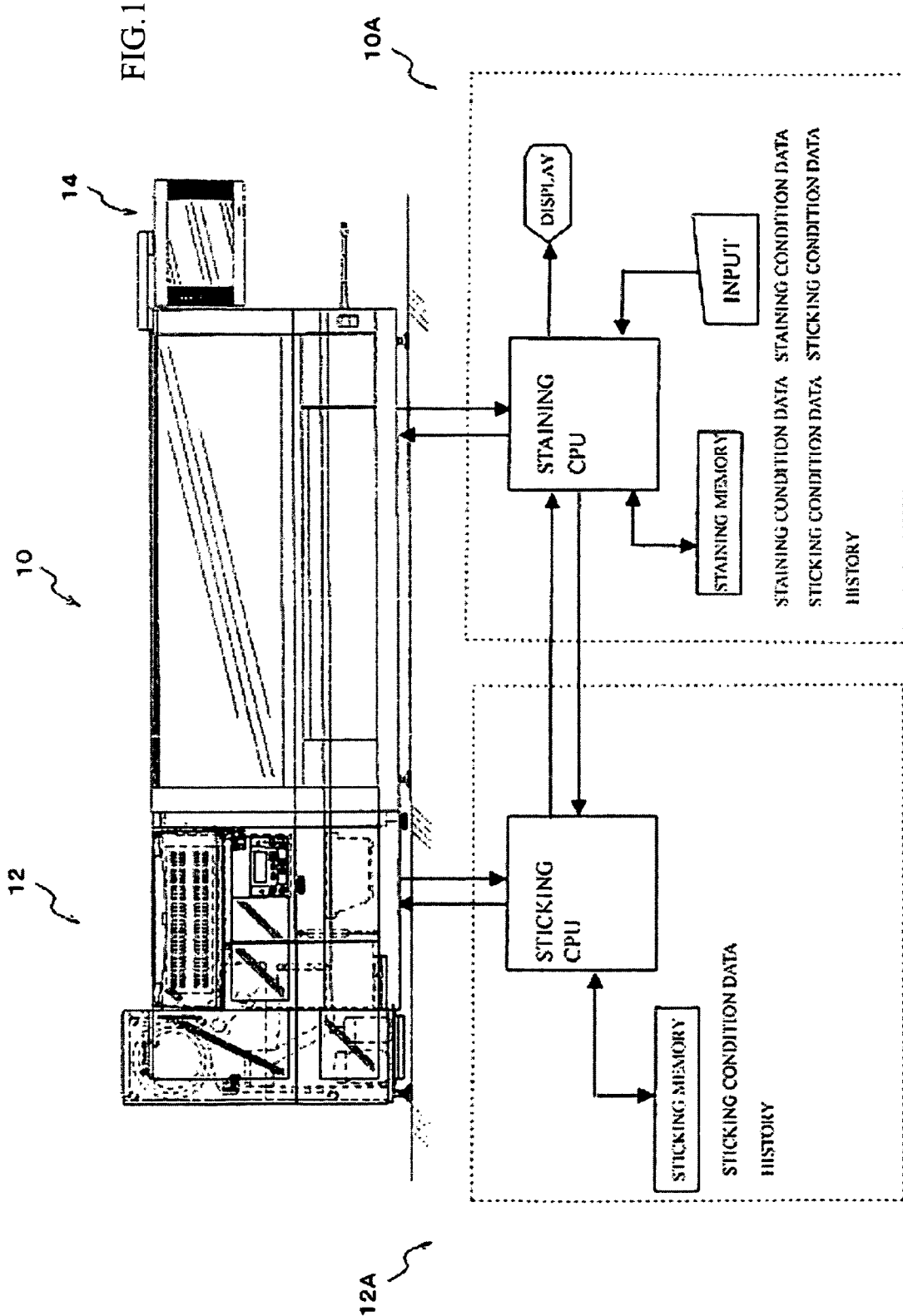
FIG. 1 is a front view of an example of the staining and sticking system of the present invention.

An example of the staining and sticking system of the present invention is shown in FIG. 1. As shown in FIG. 1, the system composed of a staining device 10 having a display monitor 14 and a sticking device 12, and the casings of the devices contact each other.

A staining control unit 10A controls the staining device 10; a sticking control unit 12A controls the sticking device 12. The staining control unit 10A and the sticking control unit 12A are interconnected so as to communicate with each other.

The staining control unit 10A comprises: a memory for storing staining condition data and sticking condition data, which are related to each of baskets, and further storing history data of staining works and sticking works; a CPU receiving signals sent from sensors, which are attached to a main body section of the staining device 10, etc. and sending a signal so as to drive the staining device 10 on the basis of the staining condition data stored in the memory; an input section for inputting the staining condition data and the sticking condition data; and a display section (e.g., the display monitor 14) displaying the staining condition data, the sticking condition data and the history data of the staining works and the sticking works.

The sticking control unit 12A comprises: a memory for storing the sticking condition data, which are related to each of the baskets and which are sent from the CPU of the staining control unit; and a CPU receiving signals sent from sensors, which are attached to a main body section of the sticking device 12, etc. and sending a signal so as to drive the sticking device 12 on the basis of the sticking condition data stored in the memory.

The history data of the sticking work performed by the sticking device 12 are sent form the CPU of the sticking control unit 12A to the CPU of the staining control unit 10A and stored in the memory of the staining control unit 10A.

Figure 2:
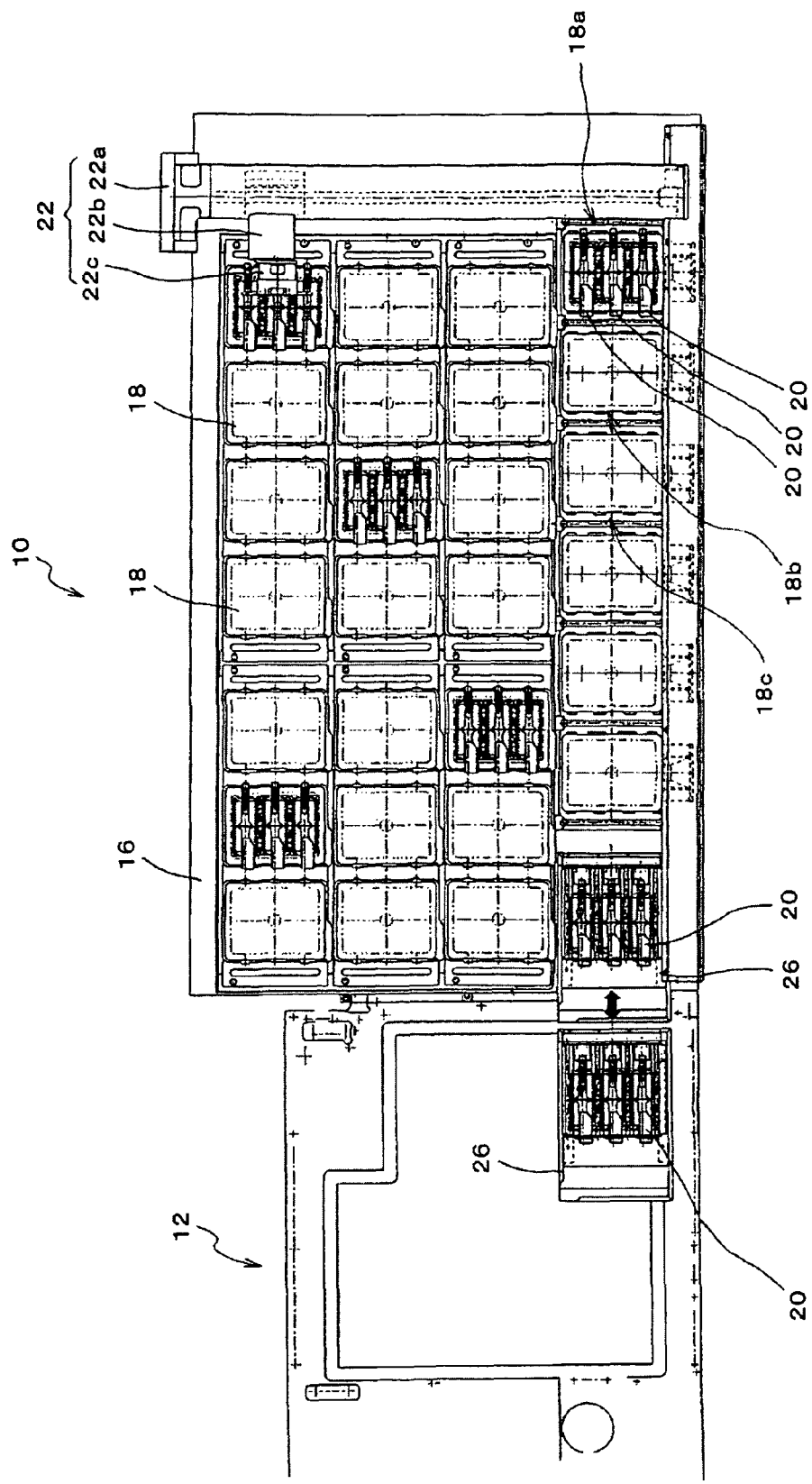
FIG. 2 is a partial plan view explaining a staining device 10 of the system shown in FIG. 1.

As shown in FIG. 2, the staining device 10 of the staining and sticking system shown in FIG. 1 has a rectangular container 16, and a plurality of tubs 18, 18 . . . , in which several kinds of liquids for staining specimens stuck on glass slides are stored, are arranged in the container. Three baskets 20, 20 and 20, each of which contains one or a plurality of glass slides with specimens, can be inserted in each of the tubs 18.

The tubs 18a, 18b and 18c of the tubs 18, 18 . . . are start tubs, so an operator initially inserts the baskets 20, each of which contains one or a plurality of glass slides with specimens to be stained, into the start tubs.

Each of the baskets 20, which has been inserted in the start tubs 18a, 18b or 18c, are inserted into the first tub 18 so as to dip the specimens stuck on the glass slides in a prescribed staining liquid or a cleaning liquid for a predetermined time period. Next, the basket 20, which has been dipped in the first tub 18, is taken out, and then transferred to and dipped into the second tub 18, in which a staining liquid or a cleaning liquid is stored. Each of the baskets 20 is sequentially dipped in a plurality of the tubs 18.

Basket transfer means 22 transfers the baskets 20. The basket transfer means 22 comprises: a lateral moving member 22a being spanned between long edges of the container 16, arranged parallel to short edges thereof and capable of moving along the long edges of the container 16; a longitudinal moving member 22b being arranged in the direction perpendicular to the lateral moving member 22a and capable of moving along the lateral moving member 22a; and a vertical moving member 22c being capable of vertically moving along the longitudinal moving member 22b.

Figure 3:
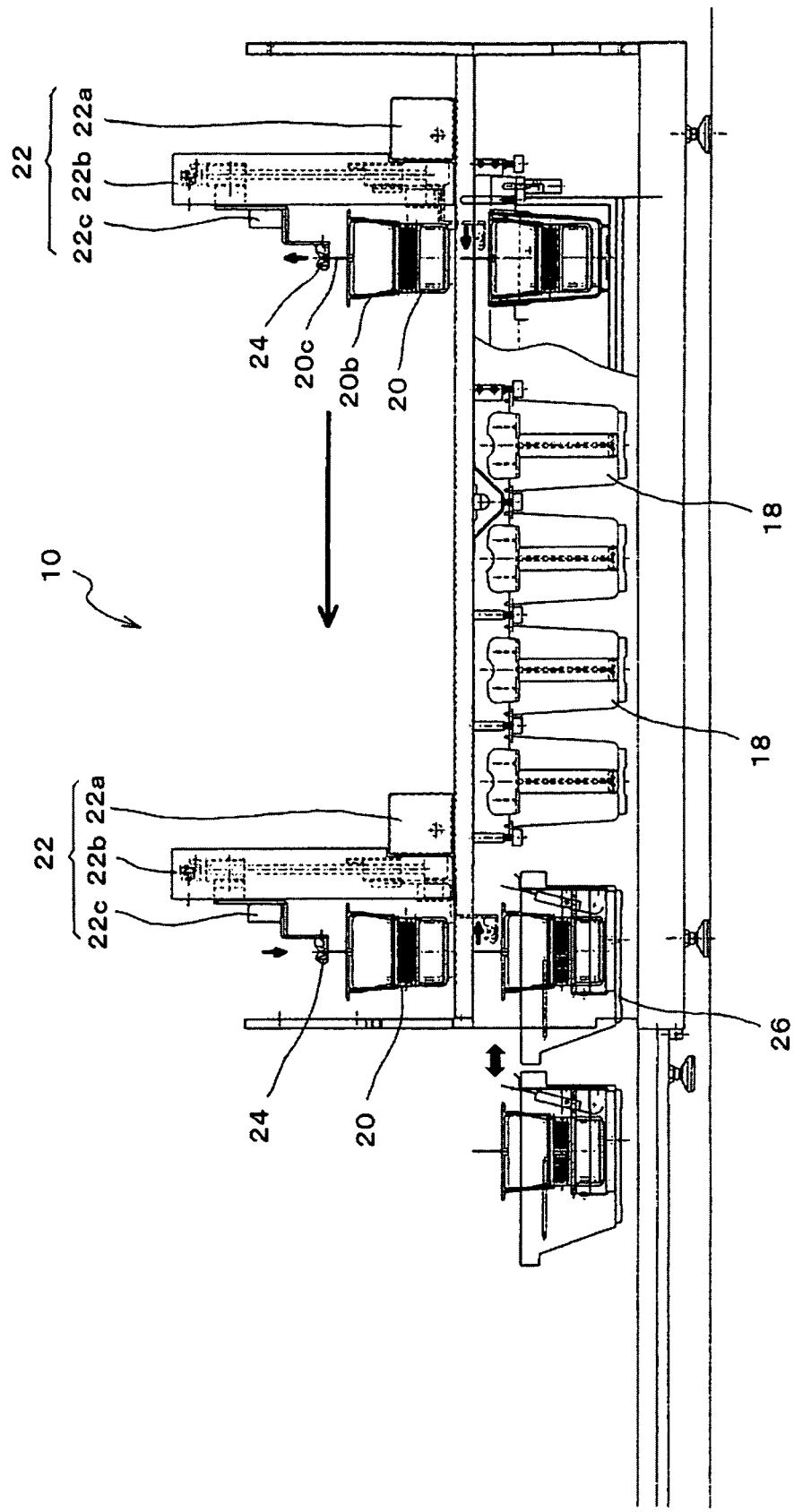
FIG. 3 is a front view explaining action of a basket transfer means 22 of the staining device 10 shown in FIG. 2.

As shown in FIG. 3, i.e., a partial sectional side view of the staining device 10, the vertical moving member 22c has a holder 24. The holder 24 suspends the baskets 20 is vertically moved together with the vertical moving member 22c, is moved along the lateral moving member 22a together with the longitudinal moving member 22b and is moved along the long edges of the container 16 together with the lateral moving member 22a.

A movable tub 26, which can enter and leave the sticking device 12 and the staining device 10, is located at a sticking device 12 side corner of the container 16 of the staining device 10 shown in FIGS. 1-3. A protective solution for protecting stained specimens is stored in the movable tub 26, and the movable tub 26 is moved into the sticking device 12 together with the baskets 20, which contain the glass slides (the glass slides with the stained specimens), in a state of being dipped in the protective solution.

When the baskets 20, which contain the glass slides with the stained specimens, are inserted into the movable tub 26, firstly the holder 24 of the vertical moving member 22c is moved to a position above the final tub 18, in which the baskets 20 containing the glass slides with the stained specimens have been dipped, by driving the lateral moving member 22a and the longitudinal moving member 22b of the basket transfer means 22.

Next, as shown in FIG. 3, the vertical moving member 22c is moved downward so as to engage the holder 24 with engage holes of baskets hooks 20c of the baskets 20, and then the vertical moving member 22c is moved upward so as to move the baskets 20 to the position above the tub 18.

Next, the baskets 20 engaged with the holder 24 is moved to a position above the movable tub 26 by driving the lateral moving member 22a and the longitudinal moving member 22b, and then the vertical moving member 22c is moved downward so as to insert the baskets 20 into the movable tub 26.

Figure 4:
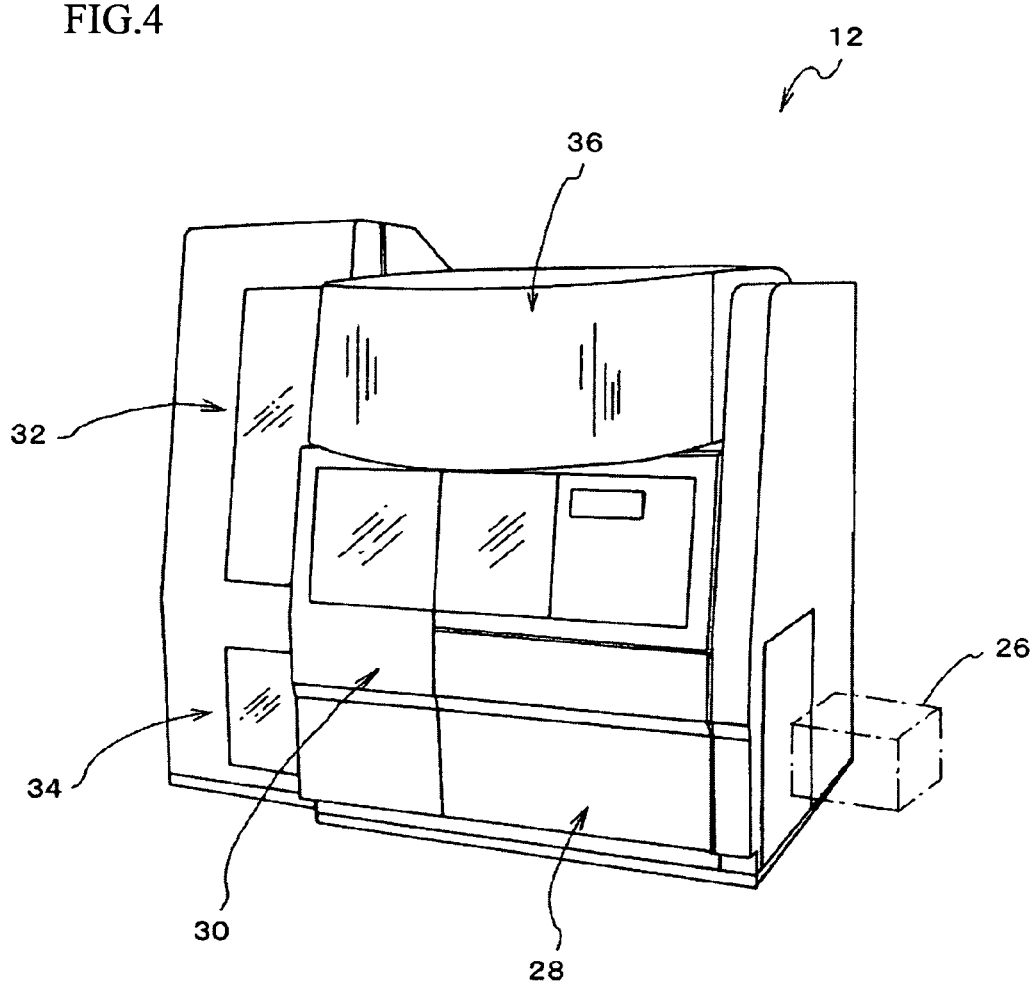
FIG. 4 is a perspective view of a sticking device 12 coordinating with the staining device 10.

The sticking device 12 located adjacent to the staining device 10 is shown in FIG. 4. The sticking device 12 shown in FIG. 4 sticks cover film pieces, in each of which an adhesive is applied to one surface, onto the specimens stuck on the glass slides.

The movable tub 26, which is transferred from the staining device 10 and in which the baskets 20 containing the glass slides with the stained specimens are dipped in the protective solution, can enter and leave the sticking device 12.

The sticking device 12 comprises: a tub setting section 28, in which the movable tub 26 is set; a main body section 30, in which a mounting medium, e.g., xylene, dissolving the adhesive applied on the one surface of the cover film piece is dropped onto the specimens on the glass slides contained in the baskets 20 transferred from the movable tub 26 to a waiting position; a cover film setting section 32 for setting a roll of a long cover film, which will be cut to form the cover film pieces having a prescribed length; a bottle setting section 34, in which a bottle storing the mounting medium to be dropped onto the specimens on the glass slides is set; and a basket accommodating section 36 for accommodating the baskets 20 containing the glass slides with the specimens covered with the cover film pieces.

Figure 5:
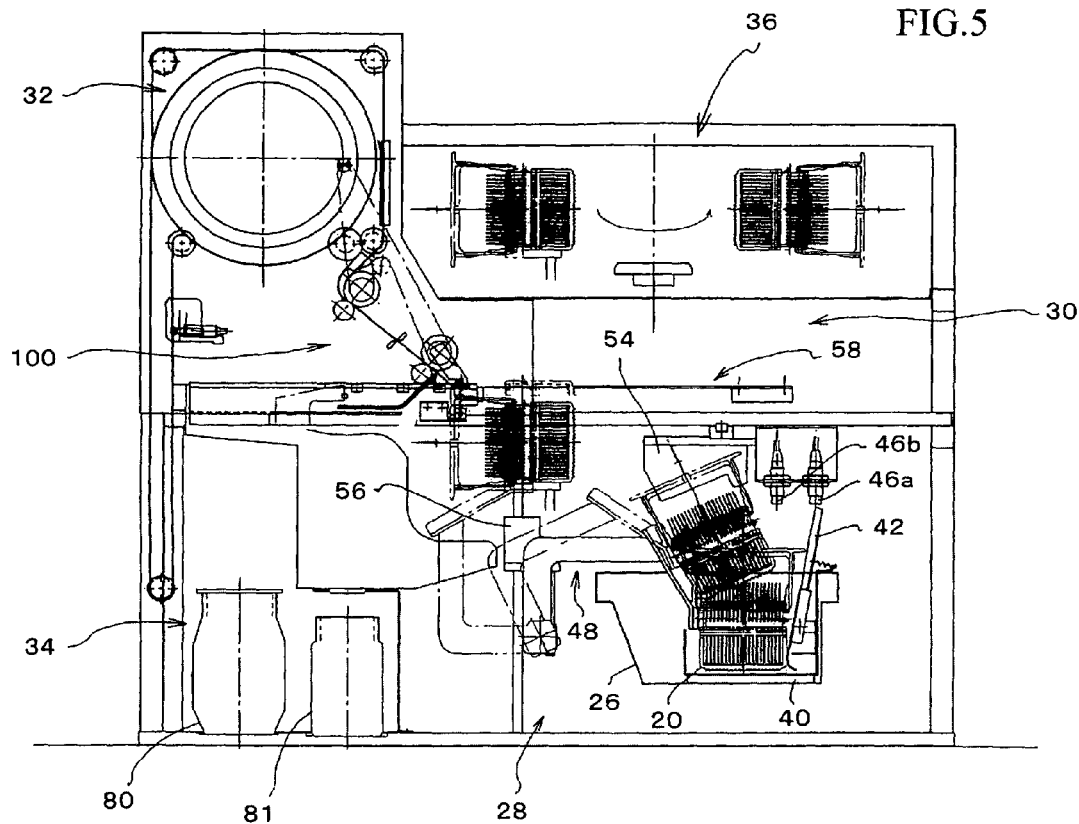
FIG. 5 is a schematic view of an inner structure of the sticking device shown in FIG. 4.
Figure 6:
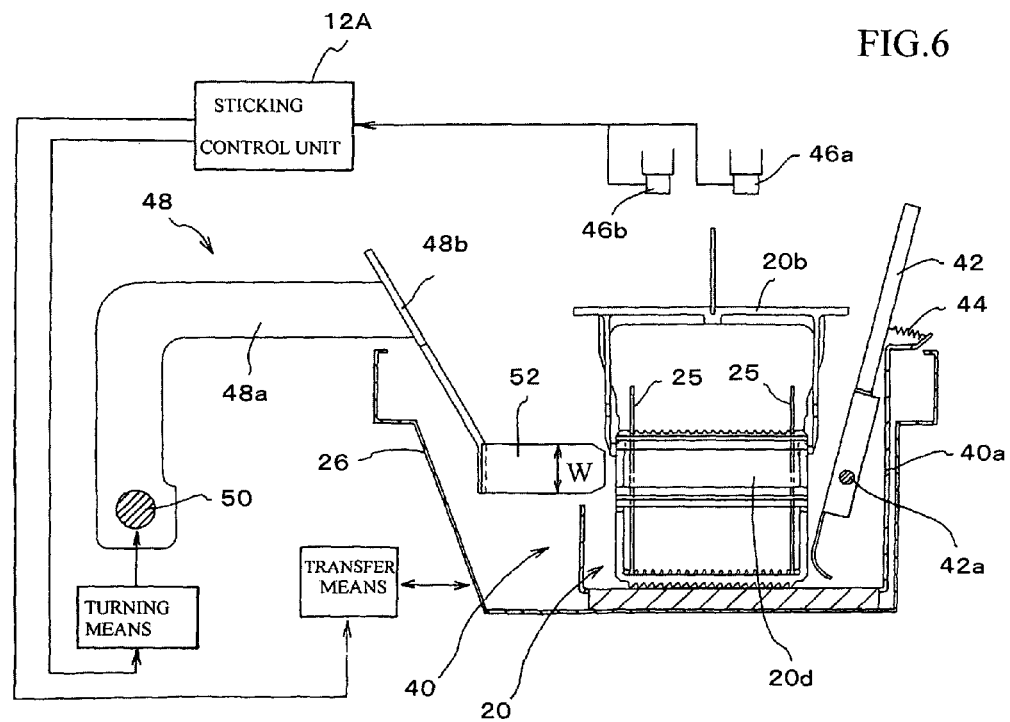
FIG. 6 is a schematic view of a tub setting section 28 shown in FIG. 4.

FIG. 5 is a schematic view of an inner structure of the sticking device shown in FIG. 4. As shown in FIG. 6, the movable tub 26 located at the tub setting section 26 shown in FIG. 5 can be moved between the staining device 10 and the sticking device 12 by suitable means, e.g., motor, cylinder unit.

In the movable tub 26, a mounting section 40, on which the basket 20 will be mounted, is fixed to a side face of the movable tub 26 as shown in FIG. 6, and a strip-shaped member 42 is provided near a wall 40a of the mounting section 40 and can be turned about a center shaft 42a.

A spring 44, which biases one end of the strip-shaped member 42 toward the wall 40a, is provided between an upper end part of the wall 40a and the one end of the strip-shaped member 42; the other end of the strip-shaped member 42 is turned toward the baskets 20 on the mounting section 40 so that it is moved away from the wall 40a until contacting the baskets 20.

Sizes of the baskets 20 depend on number of containable glass slides. Thus, sensors 46a and 46b for detecting the one end of the strip-shaped member 42 are provided above the movable tub 26 having the strip-shaped member 42 and are separately placed in the moving direction of the movable tub 26. In the sticking device 12, the sensor 46b is located on the inner side with respect to the sensor 46a.

Figure 7:
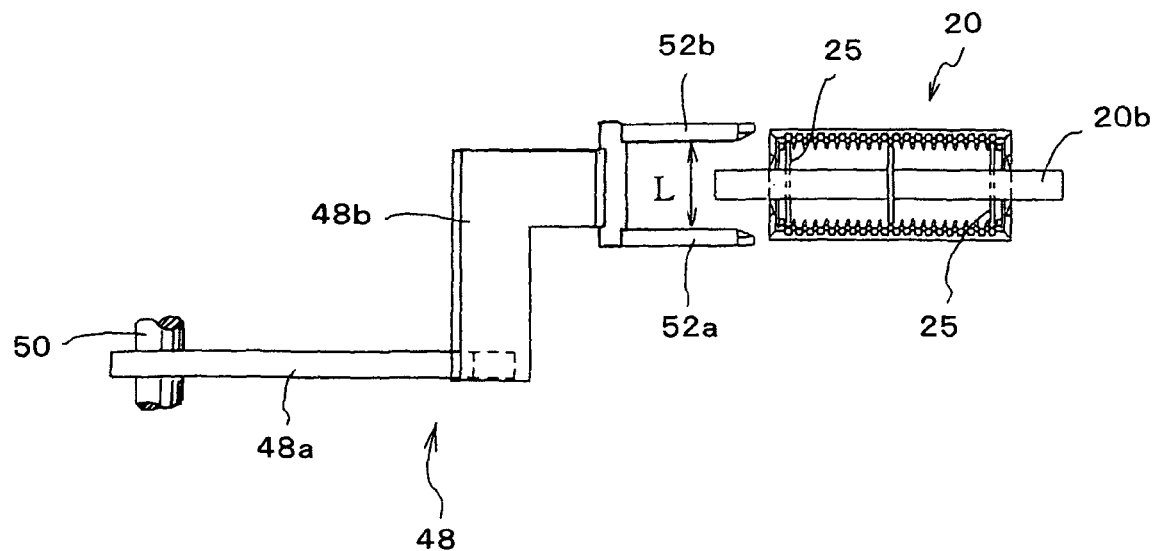
FIG. 7 is an explanation view explaining a relationship between a basket 20 inserted in a movable tub 26 and U-shaped claw sections 52a and 52b, which are provided to an arm 48 of the basket 20.

As shown in FIG. 5, a turning arm 48, which is constitute by L-shaped members 48a and 48b shown in FIGS. 6 and 7 and capable of tuning about a rear end shaft 50, is provided near the movable tub 26. U-shaped claw sections 52a and 52b are provided to a front end of the arm 48. As shown in FIG. 7, the claw sections 52a and 52b are separated with a clearance L, in which the basket 20 can be inserted; as shown in FIG. 6, the claw sections 52a and 52b having a width W can be inserted in grooves 20d and 20d of the basket 20.

Means for turning the arm 48, e.g., motor, and the means for transferring the movable tub 26 are controlled by the sticking control unit 12A, which receives signals from the sensors 46a and 46b.

The movable tub 26 is transferred from the staining device 12 to the inside of the tub setting section 28 shown in FIGS. 6 and 7, and then the arm 48 is turned to a position at which the claw sections 52a and 52b can be inserted into the grooves 20d and 20d of the basket 20 mounted on the mounting section 40 of the movable tub 26.

Next, the movable tub 26 is moved toward the claw sections 52a and 52b by the transfer means so as to insert the basket 20 in the clearance between the claw sections 52a and 52b, and only the movement of the basket 20 is stopped.

The basket 20, whose movement caused by transferring the movable tub 26 is stopped by the claw sections 52a and 52b of the arm 48, presses the other end of the strip-shaped member 42, which is moved together with the movable tub 26, in the direction opposite to the biasing direction of the spring 44.

With this action, the strip-shaped member 42 is turned against the elasticity of the spring 44, the one end of the strip-shaped member 42 is moved toward the sensor 46a, and the sensor 46a sends the detection signal to the sticking control unit 12A.

Upon receiving the detection signal from the sensor 46a, the sticking control unit 12A judges that the detected basket 20 is larger than the basket 20 to be detected by the sensor 46b, and the control unit restrains the following action.

Note that, in case that no sensors 46a and 46b detect the one end of the strip-shaped member 42, the sticking control unit 12A judges that no basket 20 is inserted in the movable tub 26, and the control unit stops the following action.

Figure 8:
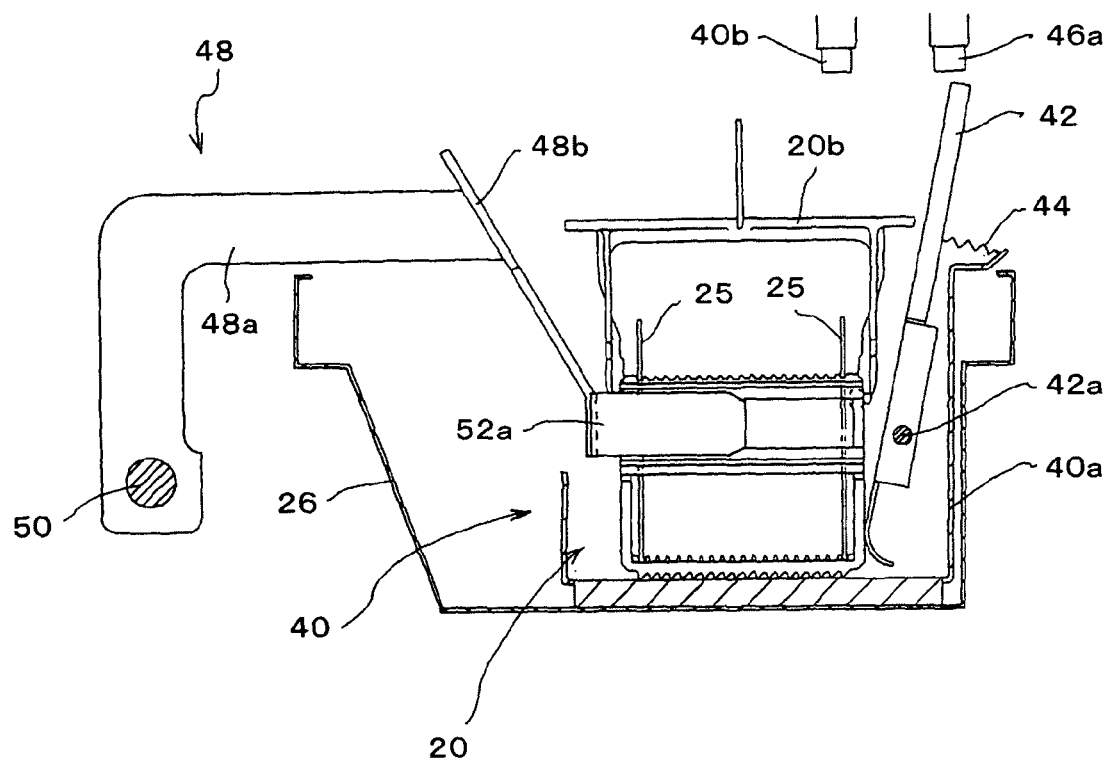
FIG. 8 is an explanation view showing a state, in which the movable tub 26 is moved to insert the basket 20 in a space between the claw sections 52a and 52b of the arm 48.

As shown in FIG. 8, when the claw sections 52a and 52b are inserted into the grooves 20d and 20d of the basket 20, which is mounted on the mounting section 40 of the movable tub 26 and which has a turnable handle 20b, and the one end of the strip-shaped member 42 is detected, the sticking control unit 12A sends a signal for driving the turning means so as to turn the arm 48 as shown in FIG. 5.

By turning the arm 48, the basket 20 held by the claw sections 52a and 52b is taken out from the movable tub 26 and turned until horizontalizing the contained glass slides 25, 25 . . . .

While the turning action, the turning action is once stopped so as to move a handle pusher 54 shown in FIG. 5 in the direction perpendicular to a paper surface of FIG. 5, so that the handle 20 of the basket 20 is turned down. By tuning down the handle 20b, taking out the glass slides 25, 25 . . . from the basket 20 and/or inserting the same thereinto is not interfered with the handle 20b.

The basket 20, whose handle 20b has been turned down, is turned until horizontalizing the contained glass slides 25, 25 . . . , and then mounted on an elevating table 56, which can be moved in the vertical direction, and upwardly moved to the waiting position.

Figure 9:
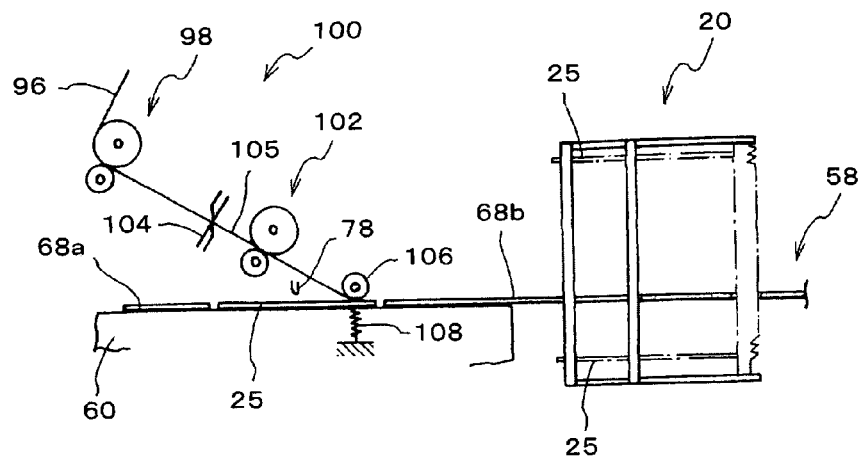
FIG. 9 is a schematic view of a main body section 30 of the sticking device 12 shown in FIG. 4.

Each of the glass slides 25, 25 . . . contained in the basket 20 located at the waiting position is transferred onto a horizontal table 60, as shown in FIG. 9, by a transfer unit 58 of the main body section 30 of the sticking device 12. The glass slide 25 on the horizontal table 60 is moved to a prescribed position of the horizontal table 60 by the transfer unit 58, and then restored in the initial place of the basket 20 located at the waiting position.

Figure 10:
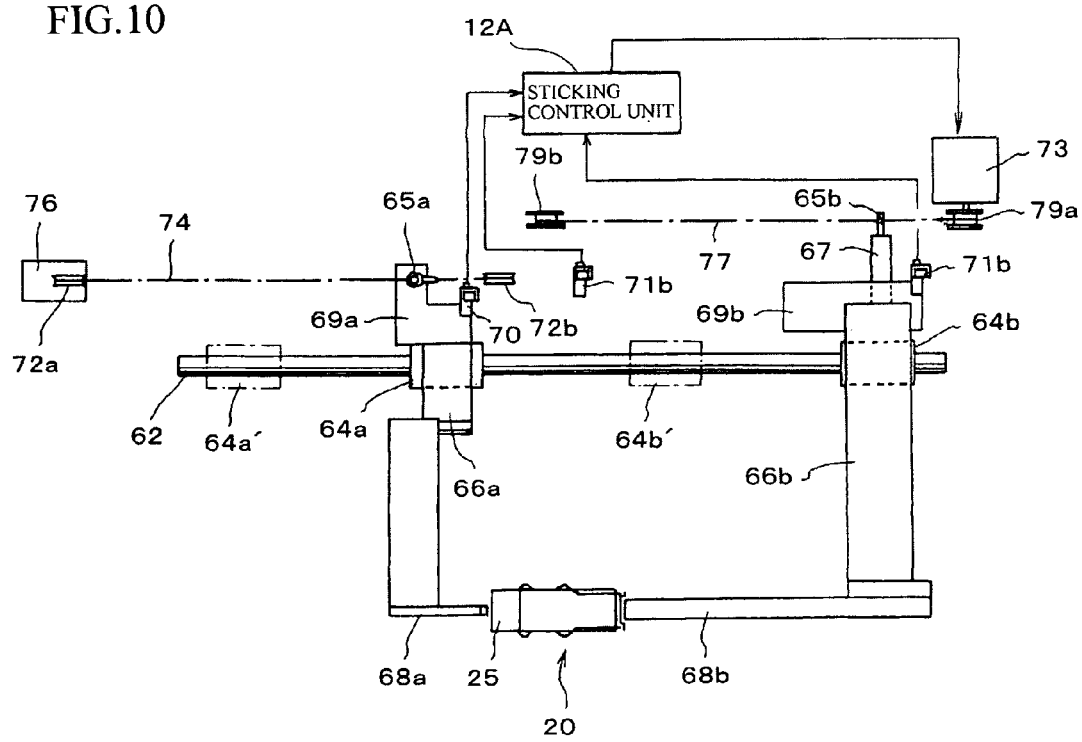
FIG. 10 is a schematic view of transfer means, which is provided to the main body section 30 and which transfers a glass slide 25 contained in the basket 20.

A transferring device shown in FIG. 10 may be used as the transfer unit 58. In the transferring device shown in FIG. 10, one ends of plate members 66a and 66b are respectively fixed to sliders 64a and 64b, which are slidably attached to a guide member 62, and detection plates 69a and 69b are respectively attached to the one ends thereof. A push ejector 68b, which ejects the glass slide 25 from a prescribed position of the basket 20 to the prescribed position of the horizontal table 60, and a return ejector 68a, which returns the glass slides 25 ejected by the push ejector 68b, to the initial position of the basket 20, are respectively provided to the other ends of the plate members 66a and 66b.

A belt 77 engaged with pulleys 79a and 79b is fixed to a member 67, which is extended from the one end of the plate member 66b, by a fixing member 65b, and the pulley 79a is rotated in the normal direction and the reverse direction by a motor 73, which is controlled by the sticking control unit 12A. With this structure, the plate member 66b is moved, by the motor 73, along the guide member 62, and the push ejector 68b is also moved along the guide member 62.

On the other hand, the plate member 66a is moved by a wire 74, which is engaged with pulleys 72a and 72b and fixed by a fixing member 65a provided to the detection plate 69a attached to the one end of the plate member 66a, and a balancer 76, which is suspended from an end of the wire 74 on the pulley 72a side.

Figure 11:
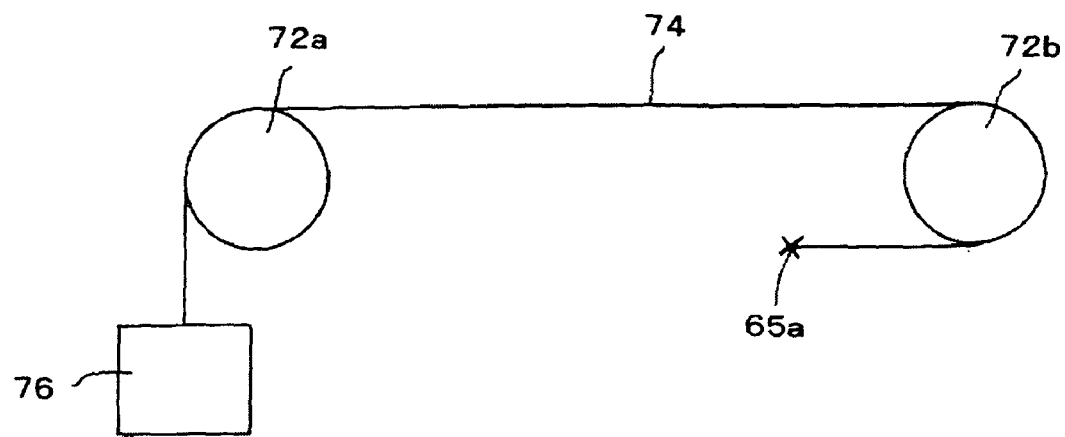
FIG. 11 is an explanation view of a balancer 76 provided to the transfer means.

As shown in FIG. 11, the balancer 76 is suspended from the pulley 72a side end of the wire 74 engaged with the pulleys 72a and 72b, and the pulley 72b side end thereof is fixed to the fixing member 65a of the detection plate 69a. With this structure, a force biasing toward the pulley 72b is applied to the plate member 66a and the return ejector 68a.

Figure 12:
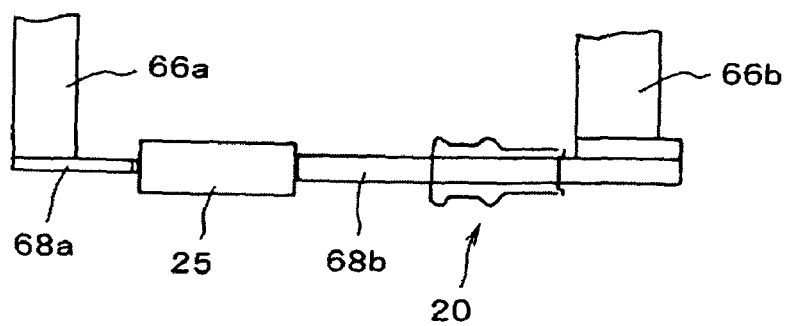
FIG. 12 is an explanation view showing a state, in which the glass slide 25 is taken out from the basket 20 by the transfer means.

Therefore, as shown in FIG. 12, the glass slide 25 with the stained specimen, which was contained in the basket 20 located at the waiting position, is clamped by the ejectors 68a and 68b and transferred onto the horizontal table 60 and moved in the predetermined direction.

Since the glass slide 25 is clamped between the ejectors 68a and 68b and transferred, a weight of the balancer 76 is suitably adjusted so as not to stop the transfer movement and break the glass slide 25.

As shown in FIG. 10, sensor 70, which detect the detection plate 69a when the front end of the return ejector 68a reaches a position close to the basket 20 located at the waiting position, are sensor 70, which detect the detection plate 69a.

Further, a right sensor 71a and a left sensor 71b, which detect the detection plate 69b, are provided, and the right sensor 71a detects the detection plate 69b when a front end of the push ejector 68b reaches a position close to the basket 20 located at the waiting position as shown in FIG. 10. On the other hand, the left sensor 71b is provided to detect the detection plate 69b when the sliders 64a and 64b reach positions 64a' and 64b' shown in FIG. 10. When the left sensor 71b detects the detection plate 69b, the push ejector 68b pierces through the basket 20 and reaches the prescribed position in the horizontal table 60.

In the sticking control unit 12A, when the glass slide, which has been contained in the basket 20 located at the waiting position, is transferred from the basket 20 to the horizontal table 60, the drive signal is sent from the sticking control unit 12A to the motor 73 so as to rotate the motor in the normal direction and make the front end of the push ejector 68b contact and push one end of the glass slide 25, so that the glass slide 25 is transferred from the basket 20 to the horizontal plate 60.

The glass slide 25, which has been pushes out from the basket 20 by the push ejector 68b, is moved away from the basket, by the push ejector 68b, against a force of the balancer 76, which is applied by making the front end of the return ejector 68a contact the other end of the glass slide. At that time, the plate member 66b is moved toward the left sensor 71b, so that the detection signal of detecting the detection plate 69b, which is sent from the right sensor 71a to the sticking control unit 12A, is turned off; the detection plate 69a of the plate member 66a is also moved, so that the detection signal of detecting the detection plate 69a, which is sent from the sensor 70 to the sticking control unit 12A, is also turned off.

When the detection plate 69b of the plate member 66b reaches a detection point and is detected by the left sensor 71b, the glass slide 25 is moved to the prescribed position in the horizontal table 60 by the push ejector 68b as shown in FIG. 9. Upon receiving the detection signal of detecting the detection plate 69b from the left sensor 71b, the sticking control unit 12A stops the motor 73 and rotates the motor in the reverse direction.

Therefore, the push ejector 68b, which contacts the glass slide 25 whose front end is pushed by the return ejector 68a, is moved toward the basket 20.

The push ejector 68b passes through the basket 20, the glass slide 25 is restored at the initial position in the basket 20, and then the sticking control unit 12A stops the reverse rotation of the motor 73 by receiving the detection signal of detecting the detection plate 69b from the right sensor 71a.

In case that the glass slide 25 is not located at the predetermined position in the basket 20 located at the waiting position, even if the detection plate 69b of the plate member 66b is not detected by the right sensor 71a, the detection plate 69a of the plate member 66a is not detected by the sensor 70. Therefore, even if the detection signal of the right sensor 71a is turned off, the sticking control unit 12A judges that no glass slide 25 is stored at the predetermined position in the basket 20 when the detection signal of the sensor 70 is turned on and transfers the next glass slide 25 from the basket 20.

The glass slide 25, which has been transferred from the predetermined position in the basket 20 to the horizontal table 60, is moved to the prescribed position by the transfer unit 58, a mounting medium is dropped onto the stained specimen on the glass slide 25 from a metal nozzle 78 as shown in FIG. 9 and a cover film piece is stuck thereonto while the glass slide is transferred from the prescribed position to the initial position in the basket 20 located at the waiting position.

Figure 13:
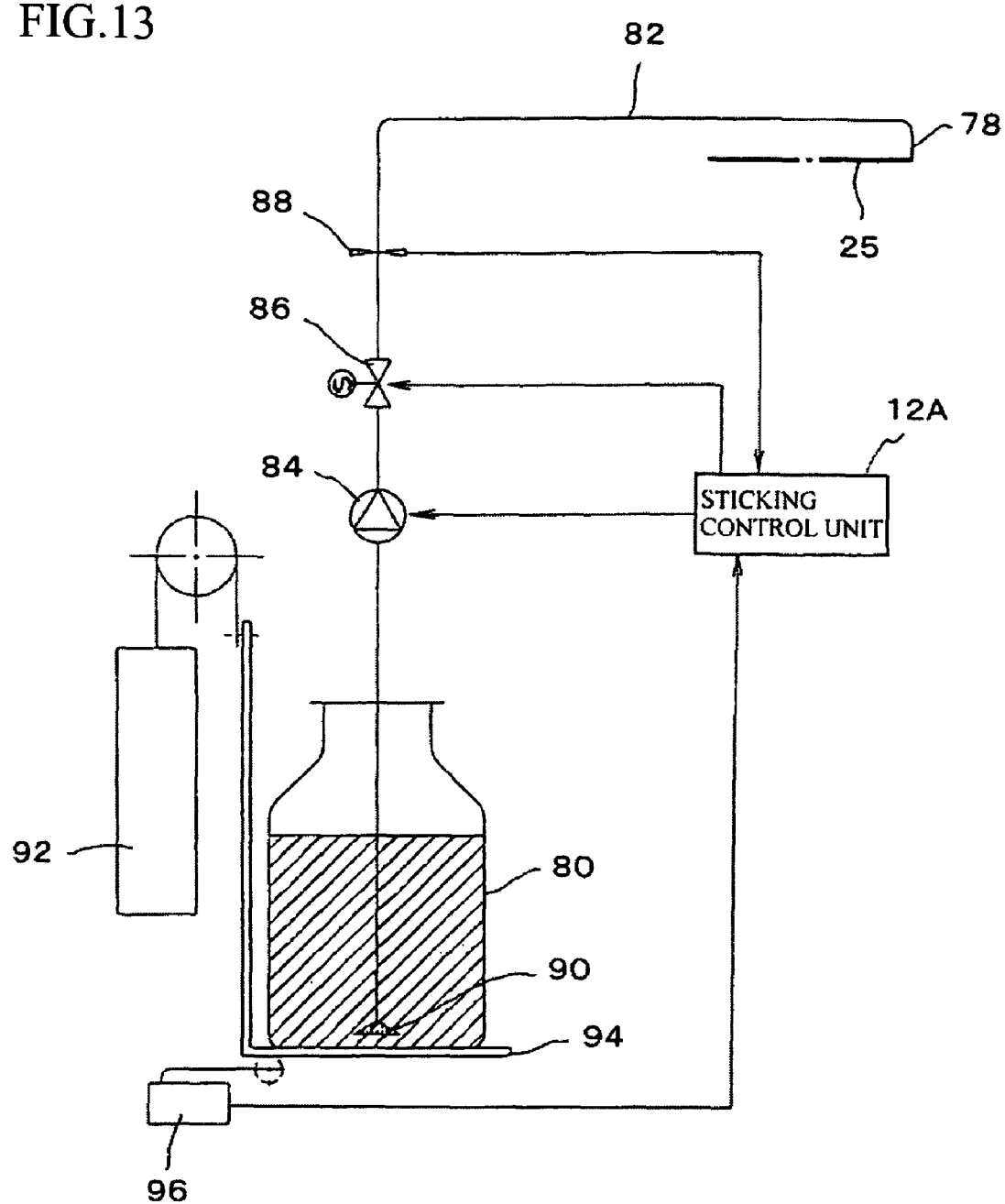
FIG. 13 is a schematic view of means for feeding a mounting medium onto the glass slide 25 transferred by the transfer means.

As shown in FIG. 13, a metal nozzle 78 is connected to means for feeding the mounting medium. As shown in FIG. 5, the feeding means has: a transparent tube 82, which introduces the mounting medium stored in a bottle 80 set in the bottle setting section 34 of the sticking device 12 shown in FIG. 5 to the metal nozzle 78, and a pump 84, an electromagnetic valve 86 and a bubble detection sensor 88 are provided to the tube 82 in that order from the bottle 80.

The pump 84 and the electromagnetic valve 86 are controlled by the sticking control unit 12A, and the bubble detection sensor 88 sends a bubble detection signal to the sticking control unit 12A when a bubble is detected in the tube 82.

A filter 90 is attached to a front end part of the tube 82, which is inserted in the bottle 80, so that sucking dusts, which have been contained in the bottle 80, into the tube 82 can be prevented when the bottle 80 is exchanged.

The bottle 80 is mounted on a table 94, to which an upward force is applied by a weight 92 whose weight is equal to the sum of a weight of the tare of the bottle 80 and a weight of the mounting medium stored in the bottle 80. Since the table 94 is moved upward and downward by the weight of the mounting medium stored in the bottle 80, the amount of the mounting medium stored in the bottle 80 can be known by measuring the vertical position of the table 94. When the mounting medium in the bottle 80 is reduced and the table 94 is upwardly moved to a predetermined position, a detection sensor 96 sends a detection signal to the sticking control unit 12A. Upon receiving the detection signal sent from the sensor 96, the sticking control unit 12A sends a stop signal to the turning means for turning the arm 48 so as not to take out the new basket 20 from the movable tub 26.

In some cases, air is sucked into the tube 82 and bubbles are formed in the tube 82 when the bottle 80 is exchanged. The bubbles in the tube 82 vary the amount of the mounting medium to be dropped onto the glass slide 25. Upon receiving the bubble detection signal sent from the bubble sensor 88, the sticking control unit 12A drives the pump 84 so as to discharge all of the mounting medium in the tube 82 from the nozzle 78 and sends a signal for opening the electromagnetic valve 86. The mounting medium discharged from the nozzle 78 is stored in a drain bottle 81 (see FIG. 5) set in the bottle setting section 34. Upon completely discharging the mounting medium from the tube 82, the sticking control unit 12A stops the pump 84 and sends a signal for closing the electromagnetic valve 86.

In the feeding means shown in FIG. 13, a distance between the bubble detection sensor 88 and the nozzle 78 is preferably designed so as to store enough amount of the mounting medium, which is capable of encapsulating a maximum number of the specimens on the glass slides 25 contained in the basket 20 located at the waiting position. By storing enough amount of the mounting medium capable of encapsulating a maximum number of the specimens on the glass slides 25 contained in the basket 20 located at the waiting position, all of the specimens on the glass slides 25 contained in the basket 20 located at the waiting position can be securely encapsulated without running short of the mounting medium.

Note that, even if the table 94, the weight 92 and the sensor 96 are not provided, the bubble detection sensor 88 detects bubbles and sends the bubble detection signal when the mounting medium in the bottle 80 is reduced and air invades into the tube 82, a timing of exchanging the bottle 80 can be known.

The mounting medium is dropped onto the glass slides by the feeding means shown in FIG. 13, and the cover film piece is pressed thereonto by sticking means 100 shown in FIG. 9.

In the sticking means 100, a pair of feed rollers 98 and a pair of cover rollers 102 feed a long cover film 96 to the glass slide 25 as shown in FIG. 9, and the cover film 96 is cut by a cutter 104 provided between the feed rollers 98 and the cover rollers 102 so as to form cover film pieces 105 shown in FIG. 9, which have a predetermined length. The cover film piece 105 is pressed and stuck onto the glass slide 25 by a sticking roller 106. A rotary shaft of the sticking roller 106 is biased toward the horizontal table 60 by biasing means having a prescribed biasing force, e.g., spring 108, so that the cover film piece 105 can be pressed onto the glass slide 25 with a fixed force.

In the sticking means 100 shown in FIG. 9, the cutting means, e.g., cutter 104, is synchronously driven with the feeding action of the feed rollers 98 from the start of the feeding action, so that the cover film pieces 105 having the prescribed length can be formed from the cover film 96. Therefore, the length of the cover film piece 105 can be shortened by driving the cutter 104 with short time intervals from the start of the feeding action of the feed rollers 98.

A sticking-start point of the cover film piece 105, form which the cover film piece is stuck on the glass slide 25, can be adjusted by adjusting start-timing of the cover roller 102. The sticking-start point of the cover film piece 105 can be close to the one end of the glass slide 25 by starting the cover rollers 102 earlier with respect to the glass slides 25 moved on the horizontal table 60. A distance between the one end of the glass slide 25 and the sticking-start point of the cover film piece 105 may be included in the sticking condition data so as to stick the cover film piece 105 at the predetermined position.

In the sticking means 100 shown in FIG. 9, the glass slide 25, which has been contained at the prescribed position in the basket 20 located at the waiting position, is clamped between the return ejector 68a and the push ejector 68b and moved to the horizontal table 60, and the glass slide 25 is further moved away from the basket 20 by the push ejector 68b until passing the nozzle 78, then the movement of the glass slide 25 performed by the push ejector 68b is stopped.

Next, the glass slide 25 is moved toward the basket 20 by the return ejector 68a, the mounting medium is dropped when the one end of the glass slide 25 reaches a predetermined position with respect to the nozzle 78, and then a pair of the feed rollers 98 and a pair of the cover rollers 102 are driven, and the cutter 104 is driven at the prescribed timing, so that the front end of the cover film piece 105 having the prescribed length is placed at the predetermined position in the glass slide 25. The cover film piece 105, which has been placed at the predetermined position in the glass slide 25, is pressed and stuck onto the glass slide 25 by the sticking roller 106.

When the glass slide 25 is moved toward the basket 20 by the return ejector 68a, a return speed of the glass slide 25 can be controlled by adjusting a reverse rotational speed of the motor 73, which returns the push ejector 68b contacting the glass slide 25.

The long cover film 96 shown in FIG. 9 is fed from cover film feeding means of the cover film setting section 32 shown in FIG. 4.

Figure 14:
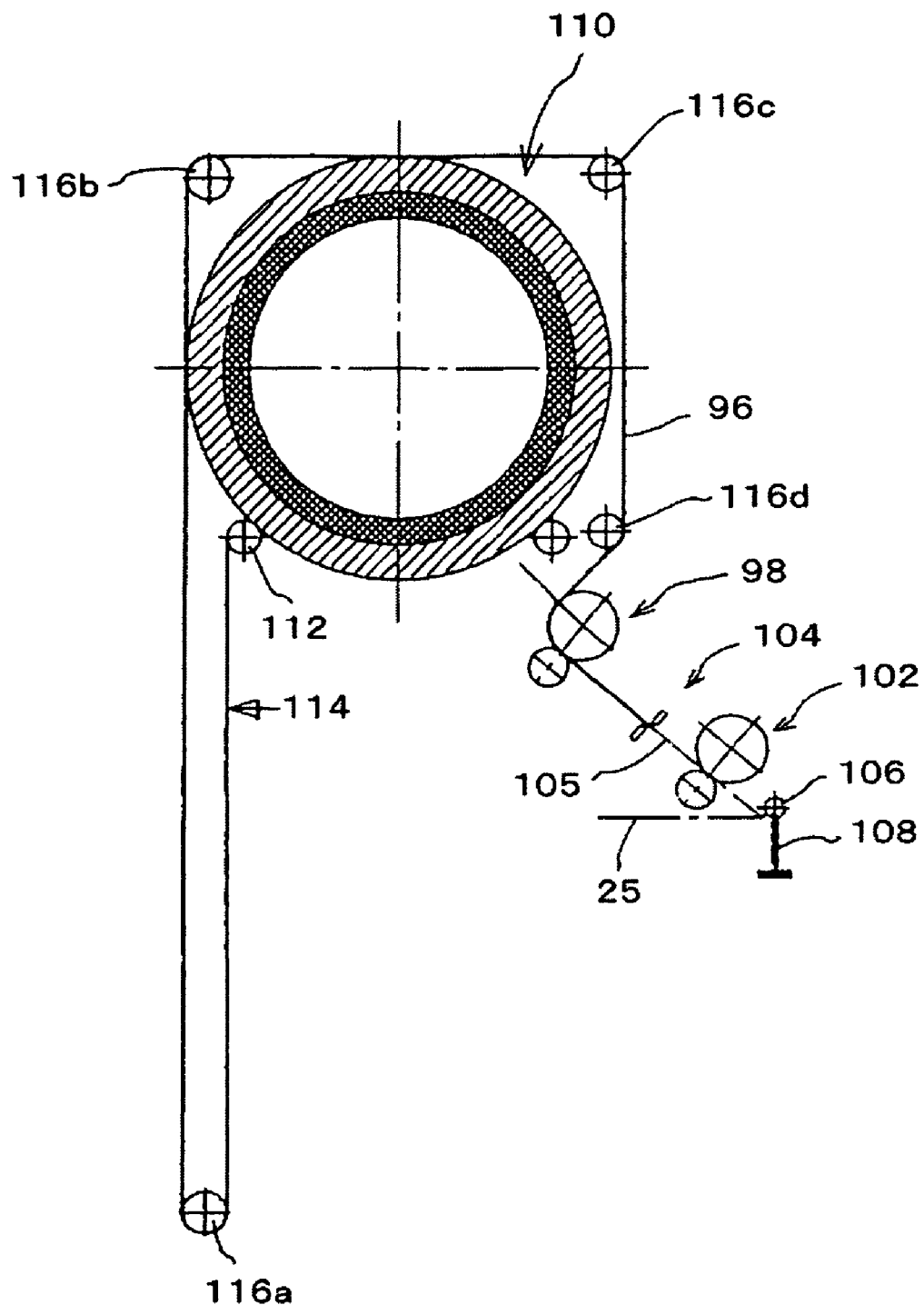
FIG. 14 is a schematic view of an example of a cover film setting section 32 of the sticking device shown in FIG. 4.

In the cover film feeding means, as shown in FIG. 14, the cover film 96 is extended from a film roll 110, in which the cover film 96 is wound, further extended by an extension roller 112 and fed to a pair of the feed rollers 98 via a sensor 114 for detecting an end of the cover film 96 and guide rollers 116a-116d provided around the film roll 110.

A length of the cover film 96 between the sensor 114 and the feed rollers 98 is designed to stick the cover film pieces 105 onto a maximum number of the glass slides 25 contained in the basket 20 located at the waiting position. By the cover film length-securing means which is constituted by the guide rollers 116a-116d provided around the film roll 110, even if the sensor 114 detects the end of the cover film 96 while treating the glass slides 25 contained in the basket 20 located at the waiting position, the cover film pieces 105 can be stuck onto all of the glass slides 25 contained in the basket 20 located at the waiting position.

Note that, the detection signal of the sensor 114 is sent to the sticking control unit 12A so as to stop taking out the new basket from the movable tub 26 and stop transferring the movable tub 26 from the staining device 10.

The glass slide 25, on which the cover film piece 105 has been stuck, is restored at the initial position in the basket 20 located at the waiting position. After the cover film pieces 105 are orderly stuck on all of the stained specimens on the glass slides 25 contained in the basket 20, the basket 20 is accommodated in the basket accommodating section 36 (see FIG. 4), which is located above the waiting position, by the elevating table 56. A basket accommodating member is provided in the basket accommodating section 36 so as to accommodate a plurality of the baskets 20.

Since the glass slides 25 with the cover film pieces 105 are restored in the basket 20, which has been contained in the basket 20, and the basket is accommodated in the basket accommodating section 36, the basket 20 is moved in one direction only, i.e., form the staining device 10 to the sticking device 12. With this structure, only the movable tub 26 is returned to the sticking device 10, so the structure of the means for transferring the movable tub 26 can be simplified.

Figure 15:
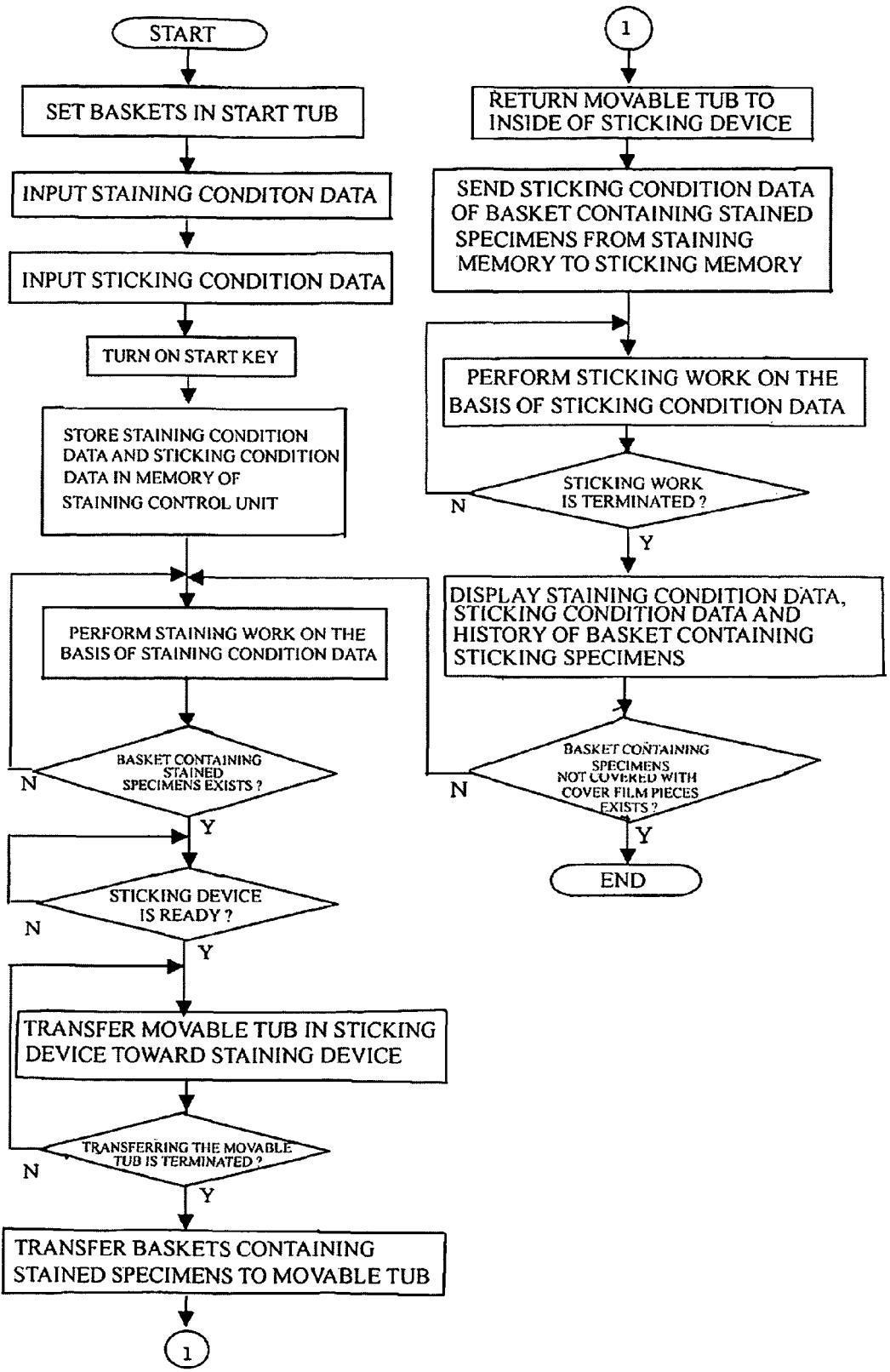
FIG. 15 is a flow chart showing action of the staining and sticking system comprising the staining device 10 and the sticking device 12.
Figure 17:
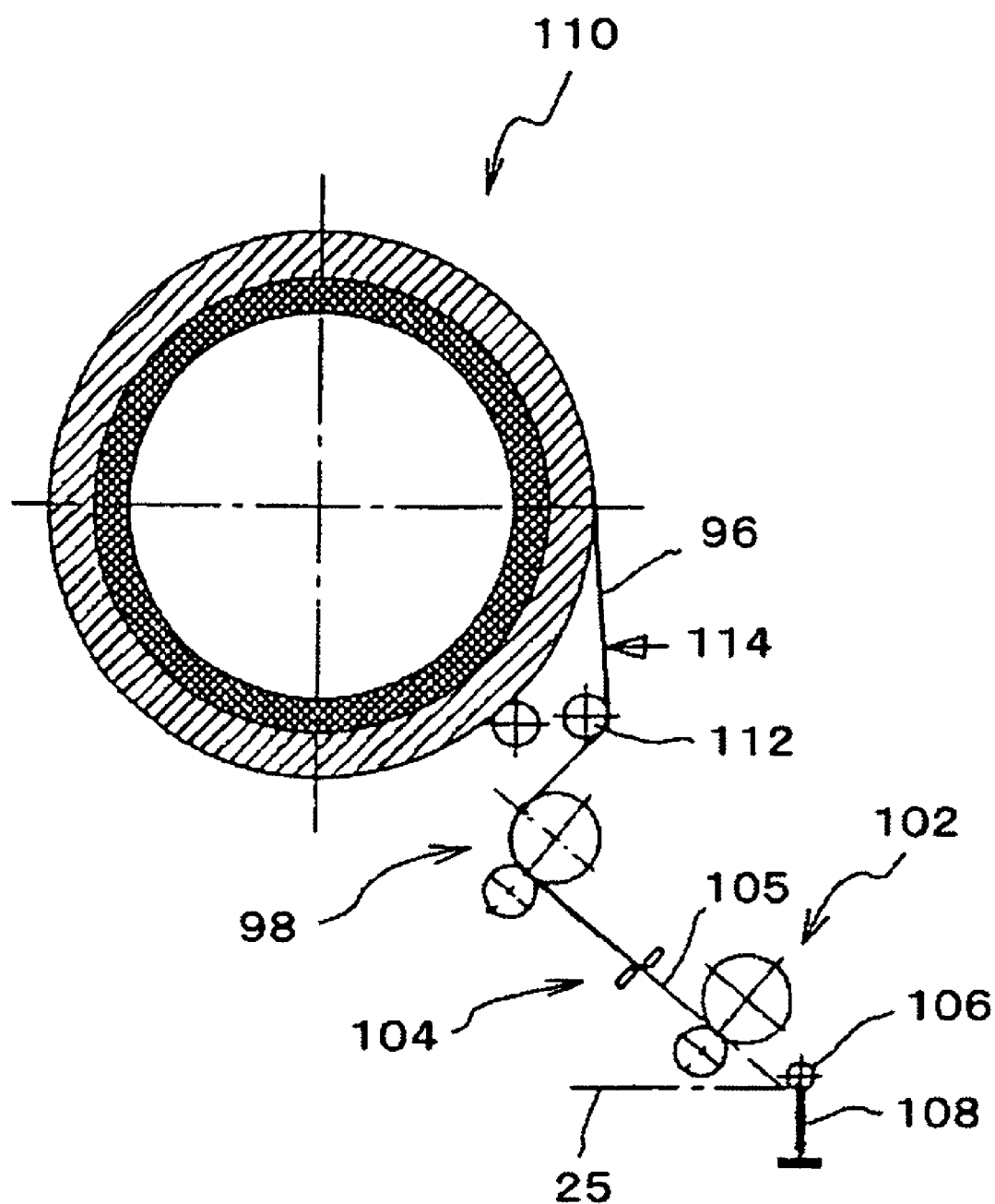
FIG. 17 is a schematic view of another example of the cover film setting section 32.

Next, the action of the staining and sticking system comprising the staining device 10 and the sticking device 12, which are shown in FIGS. 1-14, will be explained with reference to a flow chart of FIG. 15.

Firstly, the baskets 20, each of which contains one or a plurality of the glass slides 25 with the specimens, are set in the start tubs 18a, 18b and 18c (see FIG. 2). Three baskets 20 can be contained in each of the start tubs 18a, 18b and 18c.

After the baskets 20 are inserted in at least one of the baskets 20, the staining condition data and the sticking condition data are inputted to the input section of the sticking control unit 10A.

Examples of the staining condition data and the sticking condition data are shown in FIG. 16A. The staining condition data and the sticking condition data shown in FIG. 16A are applied to a case, wherein the baskets 20 are set in all of the start tubs 18a, 18b and 18c. In this case, the staining condition data including the selected tubs 18, 18 . . . provided in the container 16, dipping order and a dipping time period are inputted for each of the baskets 20 set in the start tubs 18a, 18b and 18c.

The sticking condition data including an amount of the mounting medium, which can be adjusted by adjusting a rotation number of the pump 84, a sticking speed, which can be adjusted by adjusting the return speed of the return ejector 68a, and the length of the cover film piece, which can be adjusted by controlling the cutter 104 cutting the cover film 96, are inputted for each of the baskets 20. The amount of the mounting medium and the sticking speed are divided into a plurality of stages, the stages are previously numbered, and the numbers are inputted as the sticking condition data.

By the sticking condition data, even if a plurality of the glass slides with the specimens are contained in the basket 20, the specimens on the glass slides contained in the basket can be covered with the cover film pieces under the same sticking conditions.

Note that, correcting the sticking condition data, which have been inputted with the staining condition data, can be performed by the time of starting the sticking work performed by the sticking device.

After inputting the staining condition data and the sticking condition data, a start key is turned on, and then the staining condition data and the sticking condition data, which have been inputted to the input section and which are related to each of the baskets 20, are stored in the memory of the staining control unit 10A. At that time, the CPU of the staining control unit 10A determines order of performing the staining works of the baskets 20 (or order of terminating the staining work of the baskets 20) on the basis of the number of the tubs and the dipping time period.

Next, the specimens on the glass slides 25 contained in the basket 20 are stained, in order, on the basis of the staining condition data stored in the memory of the staining control unit 10A. Data of the performed staining works are also related to the baskets 20 and stored in the memory as the history data.

Terminating the staining work of the basket 20 is judged when the actual dipping time period of the basket 20 in the final tub, which is defined as the staining condition data, is passed over the scheduled time period. The basket 20 whose staining work has been terminated can be identified on the basis of the order data stored in the memory of the staining control unit 10A.

In some cases, the new baskets 20 are inserted into the vacant start tubs 18a, 18b or 18c before starting or terminating the staining work of the baskets 20, which have been set in the start tubs 18a, 18b or 18c. In this case, when the start key is turned on, the CPU of the staining control unit 10A determines the order of performing the staining works of the baskets 20 (or the order of terminating the staining work of the baskets 20), once again, on the basis of staining condition data of the new baskets 20, which have been inputted to the input section, and the sticking condition data of the baskets 20, which have been stored in the memory of the staining control unit 10A, before starting or while performing the staining work, and the determined order is restored in the memory.

Therefore, in this case too, the basket 20 whose staining work has been terminated can be identified on the basis of the order data stored in the memory of the staining control unit 10A.

When the basket 20, whose specimens have been completely stained, exists and the sticking device 12 is ready (the sticking work is not performed in the sticking device 12), the sticking control unit 12A sends a signal so as to move the movable tub 26 in the sticking device 12 to inside of the container 16 of the staining device 10. The protective solution for protecting the stained specimens on the glass slides 25 is stored in the movable tub 26.

When the movement of the movable tub 26 toward the staining device 10 is terminated, the baskets 20, whose specimens have been completely stained, are inserted in the container 16 in the state of dipping the protective solution. Then, the movable tub 26, in which the baskets 20 containing the stained specimens have been inserted, is returned to inside of the sticking device 12.

At that time, the sticking condition data of the baskets 20 containing the stained specimens, which have been stored in the memory of the staining control unit 10A, are sent to the memory of the sticking control unit 12A, and the cover film pieces are stuck on the stained specimens on the glass slides 25 contained in the basket 20 on the basis of the sticking condition data.

The sticking condition data relating to the basket 20, which contains the stained specimens, are sent from the staining control unit 10A to the sticking control unit 12A by the time of firstly taking out the glass slide from said basket 20, preferably by the time of firstly taking out the glass slide from said basket 20 after feeding the basket 20 to the sticking device 12 so as to reduce memory capacity of the memory of the sticking control unit 12A.

Of course, the memory capacity of the memory of the sticking control unit 12A may be increased, the sticking condition data of the basket 20 may be sent to the sticking control unit 12A when the staining work is started, and the sticking condition data relating to the fed basket 20 are read from the memory of the sticking control unit 12A when the cover film pieces are stuck onto the stained specimens.

The cover film pieces are stuck onto the specimens on the glass slides 25 contained in the basket 20 on the basis of the sticking condition data stored in the memory of the sticking control unit 12A. When the cover film pieces are stuck on all of the specimens on the glass slides 25 contained in the basket 20, the monitor 14 displays the staining condition data, the sticking condition data and the work history of the basket 20.

Next, the staining condition data, the sticking condition data and the history data stored in the memory of the staining control unit 10A are examined so as to check if there are untreated baskets in the staining and sticking system or not. If there are any untreated baskets in the system, the staining work is restarted; if there are no untreated baskets therein, the staining and sticking works are terminated.

In the above described embodiment, the cover film pieces can be uniformly stuck onto the stained specimens on the glass slides, which are contained in the basket 20, by performing the sticking works on the basis of the sticking condition data relating to said basket.

In the sticking device 12 of the staining and sticking system shown in FIG. 1, as shown in FIG. 9, the cover film pieces are stuck onto the stained specimens on the glass slides 25, 25 . . . , which are contained in the basket 20, in order.

As shown in FIG. 16B, the sticking condition data inputted to the staining control unit 10A are optimum data for each of the stained specimens on the glass slides 25 contained in the basket 20, so that the cover film piece can be stuck onto each of the stained specimens on the glass slides 25, which are contained in the basket 20, under the independent optimum sticking conditions respectively.

The cover film length-securing means, which is constituted by the guide rollers 116a-116d provided around the film roll 110, extends the cover film 96 so as to secure the required length of the cover film 96, so a prescribed space must be formed in the sticking device 12. In the cover film 96 wound as the film roll 110, a mark is previously formed at a predetermined position, which is separated a predetermined distance from a terminal end; namely, the cover film pieces cut from the cover film 96 having said distance can be stuck onto all of the glass slides 25 contained the basket 20 located at the waiting position, and the mark can be detected by the sensor 114, which is provided immediately before the feed rollers 98, as shown in FIG. 15.

Further, a plurality of the baskets 20, 20 . . . may be arranged parallel in the movable tub 26. In this case, the strip-shaped members 42 must be arranged parallel in the movable tub 26.

In the sticking device 12 shown in FIGS. 4-16, the cover film pieces having the prescribed length are stuck onto the stained specimens on the glass slides 25, but the sticking device 12 may stick cover glasses onto the stained specimens on the glass slides 25 instead of the cover film pieces 105.

Figure 18:
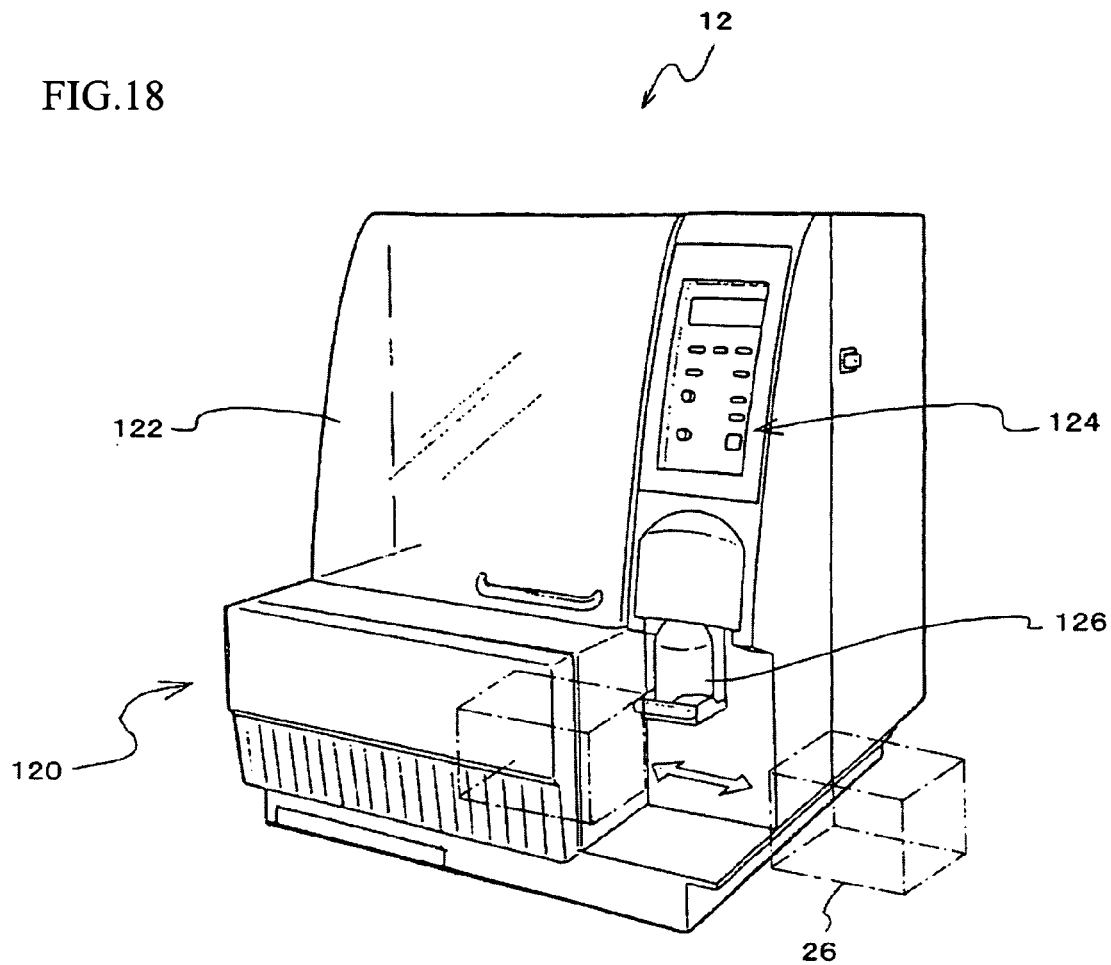
FIG. 18 is a perspective view of another sticking device 12, which can be used instead of the sticking device 12 shown in FIGS. 4-14.

A sticking device 12 shown in FIG. 18, which is disclosed in Japanese Patent Gazette No. 2001-2731, may be used to stick cover glasses onto glass slides.

In the sticking device 12 shown in FIG. 18, a transparent cover 122 of a main body part 120 can be opened and closed, and an operation panel 124 is attached to the main body part 120. Further, a container 126 storing a mounding medium is inserted in the main body part 120.

Figure 19:
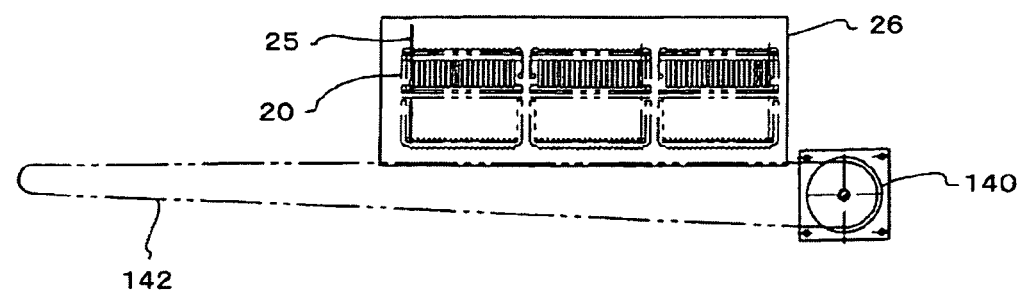
FIG. 19 is an explanation view of transfer means, which is provided to the sticking device 12 shown in FIG. 18 and which transfers the movable tub 26.

The movable tub 26 can be transferred between the main body part 120 and the staining device 10. As shown in FIG. 19, means for transferring the movable tub 26 is constituted by a motor 140 provided in the main body part 120 and a wire 142 driven by the motor 140, and a front end part of the wire 142 is extended to inside of the staining device 10.

In the staining and sticking system shown in FIGS. 1-19, at least parts of the casings of the staining device 10 and the sticking device 12 are mutually contacted, but a transferring device may be provided between the staining device 10 and the sticking device 12. By providing the transferring device, the sticking device 12 can collaborate with a wide variety of staining devices 10.

The invention claimed is:

1. A staining and sticking system comprising:
a staining device for staining a sliced specimen in a predetermined color by sequentially dipping a basket, which contains one or a plurality of glass slides with the specimens, in a plurality of tubs, in which liquids for staining the specimen are stored; and
a sticking device for sticking a cover film piece or a cover glass onto the stained specimen on the glass slide, which has been taken out of the basket transferred from the staining device by transfer means,
wherein a staining control unit of the staining device and a sticking control unit of the sticking device are interconnected so as to communicate with each other,
wherein the staining control unit includes a controller having
a first memory for storing staining condition data and sticking condition data which are related to the basket, and history data of staining works and sticking works;
a first CPU receiving a signal sent from a first sensor, which is attached to a main body section of the staining device, and sending a signal to means for driving the staining device on the basis of the staining condition data stored in the first memory;
an input section for inputting the staining condition data and the sticking condition data,
the staining device sequentially dips the basket into the prescribed tubs on the basis of the staining condition data corresponding to the basket, and
wherein the sticking control unit includes a controller having
a second memory for storing the sticking condition data, which are related to the basket and sent from the first CPU of the staining control unit; and
a second CPU receiving a signal sent from a second sensor, which is attached to a main body section of the sticking device, and sending a signal to means for driving the sticking device on the basis of the sticking condition data stored in the second memory, and
sticking control unit sticks the cover film piece or the cover glass onto the stained specimen on the glass slide, which has been contained in the fed basket, on the basis of the sticking condition data, which are related to the basket transferred from the staining device and sent from the staining control unit to the sticking control unit.

2. The staining and sticking system according to claim 1, wherein the staining condition data and the sticking condition data are inputted to the staining control unit before starting the staining work.

3. The staining and sticking system according to claim 1, wherein the sticking condition data of the basket fed from the staining device are sent from the staining control unit to the sticking control unit by the time of firstly taking out the glass slide from the fed basket.

4. The staining and sticking system according to claim 1, wherein at least parts of casings of the staining device and the sticking device contact each other.

5. The staining and sticking system according to claim 1, wherein the transfer means transfers the basket, which contains the glass slide with the stained specimen, in a state of being dipped in a protective solution for protecting the specimen.

6. The staining and sticking system according to claim 1, wherein the basket, which contains the glass slide with the stained specimen, is inserted in a movable tub, in which a protective solution for protecting the specimen is stored, and transferred together with the movable tub.

7. The staining and sticking system according to claim 1, wherein a main part of the transfer means, which transfers the basket from the inside of the staining device to the inside of the sticking device, is provided in the sticking device.

* * * * *